US00PP31450P3

(12) United States Plant Patent
Meulenbroek

(10) Patent No.: US PP31,450 P3
(45) Date of Patent: Feb. 18, 2020

(54) STRAWBERRY PLANT NAMED 'FF 1503'

(50) Latin Name: ***Fragaria* x *ananassa***
Varietal Denomination: FF 1503

(71) Applicant: Egbertus Joseph Meulenbroek, Zetten (NL)

(72) Inventor: Egbertus Joseph Meulenbroek, Zetten (NL)

(73) Assignee: FRESH FORWARD HOLDING B.V., Eck en Wiel (NL)

( * ) Notice: Subject to any disclaimer, the term of this patent is extended or adjusted under 35 U.S.C. 154(b) by 0 days.

(21) Appl. No.: 15/932,822

(22) Filed: Apr. 30, 2018

(65) Prior Publication Data

US 2019/0335637 P1 Oct. 31, 2019

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
CPC ..... A01H 5/0893
See application file for complete search history.

(56) References Cited

PUBLICATIONS https://www.facebook.com/fragariaholland/posts/ff-1503-een-late-junidrager-mooie-vrucht-stevig-en-goed-van-smaakff1503-eine-sp%C3%A4/1858700764449512/; Jul. 15, 2017; 5 pages.*

* cited by examiner

*Primary Examiner* — Kent L Bell
(74) *Attorney, Agent, or Firm* — C. A. Whealy

(57) ABSTRACT

A new and distinct cultivar of Strawberry plant named 'FF 1503', characterized by its compact, upright to semi-upright plant habit; moderately vigorous to vigorous growth habit; uniform fruit ripening; medium to large conical fruits that are glossy and orange red in color; pleasant fruit aroma and sweet taste; excellent fruit postharvest longevity; and moderate resistance to *Phytophthora cactorum* and *Podosphaera aphanis*.

2 Drawing Sheets

Botanical designation: *Fragaria* x *ananassa*.
Cultivar denomination: 'FF 1503'.

BACKGROUND OF THE INVENTION

The present Invention relates to a new and distinct cultivar of Strawberry plant, botanically known as *Fragaria* x *ananassa* and hereinafter referred to by the name 'FF 1503'.

The new Strawberry plant is a product of a planned breeding program conducted by the Inventor in Eck en Wiel, The Netherlands. The objective of the breeding program was to develop new Strawberry plants with good fruit quality, ease of harvesting, good postharvest longevity and resistance to pathogens.

The new Strawberry plant originated from a cross-pollination by the Inventor in 2005 in Eck en Wiel, The Netherlands of a proprietary selection of *Fragaria* x *ananassa* identified as code number E2002-032, not patented, as the female, or seed, parent with a proprietary selection of *Fragaria* x *ananassa* identified as code number E1996-120, not patented, as the male, or pollen, parent. The new Strawberry plant was discovered and selected by the Inventor as a single plant from within the progeny of the stated cross-pollination in a controlled environment in Eck en Wiel, The Netherlands in 2007.

Asexual reproduction of the new Strawberry plant by runner cuttings in a controlled environment at Eck en Wiel, The Netherlands since 2007 has shown that the unique features of this new Strawberry plant are stable and reproduced true to type in successive generations of asexual reproduction.

SUMMARY OF THE INVENTION

Plants of the new Strawberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'FF 1503'. These characteristics in combination distinguish 'FF 1503' as a new and distinct Strawberry plant:

1. Compact, upright to semi-upright plant habit.
2. Moderately vigorous to vigorous growth habit.
3. Uniform fruit ripening.
4. Medium to large conical fruits that are glossy and orange red in color.
5. Pleasant fruit aroma and sweet taste.
6. Excellent fruit postharvest longevity.
7. Moderately resistant to *Phytophthora cactorum* and *Podosphaera aphanis*.

Plants of the new Strawberry differ primarily from plants of the female parent selection in the following characteristics:

1. Plants of the new Strawberry are more upright and not as flat globose as plants of the female parent selection.
2. Fruits of plants of the new Strawberry are conical in shape whereas fruits of plants of the female parent selection are ovoid in shape.
3. Fruits of plants of the new Strawberry are orange red in color whereas fruits of plants of the female parent selection are dark red in color.

Plants of the new Strawberry differ primarily from plants of the male parent selection in the following characteristics:

1. Plants of the new Strawberry are more vigorous than plants of the male parent selection.
2. Leaves of plants of the new Strawberry are darker green in color than leaves of plants of the male parent selection.
3. Fruits of plants of the new Strawberry are orange red in color whereas fruits of plants of the male parent selection are orange in color.

Plants of the new Strawberry can be compared to plants of *Fragaria* x *ananassa* 'Symphony', not patented. In side-by-side comparisons, plants of the new Strawberry differ primarily from plants of 'Symphony' in the following characteristics:

1. Fruits of plants of the new Strawberry are orange red in color whereas fruits of plants of 'Symphony' are red in color.
2. Seeds of plants of the new Strawberry are level with the skin surface whereas seeds of plants of 'Symphony' are slightly extruded beyond the skin surface.
3. Seeds of plants of the new Strawberry are yellow red in color whereas seeds of plants of 'Symphony' are bright yellow in color.

Plants of the new Strawberry can be compared to plants of *Fragaria* x *ananassa* 'Florence', not patented. In side-by-side comparisons, plants of the new Strawberry differ primarily from plants of 'Florence' in the following characteristics:

1. Fruits of plants of the new Strawberry are not as upright as fruits of plants of 'Florence'.
2. Fruits of plants of the new Strawberry are orange red in color whereas fruits of plants of 'Florence' are red in color.

Plants of the new Strawberry can also be compared to plants of *Fragaria* x *ananassa* 'Jive', disclosed in U.S. Plant Pat. No. 26,711. In side-by-side comparisons, plants of the new Strawberry differ primarily from plants of 'Jive' in the following characteristics:

1. Fruits of plants of the new Strawberry are more compact than fruits of plants of 'Jive'.
2. Fruits of plants of the new Strawberry are more conical and not as broad as fruits of plants of 'Jive'.
3. Fruits of plants of the new Strawberry are orange red in color whereas fruits of plants of 'Jive' are red in color.
4. Fruits of plants of the new Strawberry are more aromatic and sweeter in flavor than fruits of plants of 'Jive'.

BRIEF DESCRIPTION OF THE PHOTOGRAPHS

The accompanying colored photographs illustrate the overall appearance of the new Strawberry plant showing the colors as true as it is reasonably possible to obtain in colored reproductions of this type. Colors in the photographs may differ slightly from the color values cited in the detailed botanical description which accurately describe the colors of the new Strawberry plant.

The photograph on the first sheet is a top perspective view of typical flowering plants of 'FF 1503' grown in an outdoor nursery.

The photograph on the second sheet is a close-up view of typical developing and developed fruits of 'FF 1503'.

DETAILED BOTANICAL DESCRIPTION

The following observations and measurements describe plants grown in 2.5-liter containers during the spring and summer in a glass-covered greenhouse in Elst, Gelderland, The Netherlands and under cultural practices typical of commercial Strawberry production. During the production of the plants, day temperatures ranged from 12° C. to 23° C. and night temperatures ranged from 8° C. to 12° C. Plants were one year old when the photographs were taken and ten weeks from planting when the description was taken. In the following description, color references are made to The Royal Horticultural Society Colour Chart, 2001 Edition, except where general terms of ordinary dictionary significance are used.

Botanical classification: *Fragaria* x *ananassa* 'FF 1503'.

Parentage:

*Female, or seed, parent*.—Proprietary selection of *Fragaria* x *ananassa* identified as code name E2002-032, not patented.

*Male, or pollen, parent*.—Proprietary selection of *Fragaria* x *ananassa* identified as code name E1996-120, not patented.

Propagation:

*Type*.—By runner cuttings.

*Time to initiate roots, summer*.—About one to four days at soil temperatures about 15° C.

*Time to produce a rooted young plant, summer*.—About two to three weeks at soil temperatures ranging from 15° to 20° C.

*Root description*.—Medium in thickness, fibrous; typically cream white to white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Perennial; compact, upright to semi-upright plant habit; leaves basal; moderately vigorous to vigorous growth habit; moderate growth rate; moderately densely foliated and bushy to somewhat open canopy.

*Plant height*.—About 25 cm to 30 cm.

*Plant diameter*.—About 30 cm to 35 cm.

*Stolon texture*.—Sparsely pubescent.

*Stolon color and texture*.—Close to 144B.

Leaf description:

*Arrangement and appearance*.—Basal rosette; compound with typically three leaflets per leaf; leaves, non-variegated.

*Leaflet length*.—About 9 cm to 12 cm.

*Leaflet width*.—About 8 cm to 11 cm.

*Leaflet shape*.—Broadly ovate.

*Leaflet apex*.—Obtuse to acute.

*Leaflet base*.—Obtuse to rounded.

*Leaflet margin*.—Serrate to lobed.

*Leaflet texture and luster, upper surface*.—Pubescent; moderately glossy.

*Leaflet texture and luster, lower surface*.—Pubescent, rough; matte.

*Leaflet venation*.—Pinnate.

*Leaflet color*.—Developing leaflets, upper surface: Close to 137A. Developing leaflets, lower surface: Close to 138A. Fully expanded leaflets, upper surface: Close to between 137C and 137A; venation, close to 144C. Fully expanded leaflets, lower surface: Close to 138A; venation, close to 144C.

*Petioles*.—Length: About 9 cm to 15 cm. Diameter: About 2.5 mm to 5 mm. Texture, upper and lower surfaces: Pubescent. Color, upper and lower surfaces: Close to 145A.

Flower description:

*Flower form and flowering habit*.—Rotate flowers arranged singly at lateral apices; flowers held at the foliar plane; flowers are self-fertile.

*Fragrance*.—None detected.

*Natural flowering season*.—Plants flower in late April to early May in The Netherlands, considered early to midseason flowering.

*Flower diameter*.—About 2.5 cm to 3.5 cm.

*Flower depth* (*height*).—About 5 mm to 10 mm.

*Petals*.—Arrangement: Single whorl of six petals; petals imbricate. Length: About 8 mm to 12 mm. Width: About 8 mm to 12 mm. Shape: Round to broadly ovate. Apex: Rounded. Base: Attenuate. Margin: Entire. Texture, upper and lower surfaces: Smooth, glabrous; satiny. Color: When opening and fully opened, upper surface: Close to 155D. When opening and fully opened, lower surface: Close to 155D.

*Sepals*.—Arrangement and calyx description: Single whorl of eight to twelve sepals; calyx, star-shaped; calyx adherence is weak to moderate; sepals are orientated upwards from the fruit. Calyx length: About 1 cm to 1.5 cm. Calyx diameter: About 1 cm to 2 cm. Length: About 5 mm to 8 mm. Width: About 3 mm to 5 mm. Shape: Lanceolate to ovate. Apex: Acute. Base: Fused. Margin: Entire. Texture, upper and lower surfaces: Pubescent. Color, upper and lower surfaces: Close to 137A.

*Peduncles*.—Length: About 7 cm to 10 cm. Diameter: About 1 mm to 2 mm. Strength: Strong. Texture: Pubescent. Color: Close to 144B.

*Pedicels*.—Length: About 2 cm to 5 cm. Diameter: About 1 mm to 2 mm. Strength: Strong. Aspect: About 90° from peduncle axis. Texture: Pubescent. Color: Close to 144B.

*Reproductive organs*.—Stamens: Quantity per flower: About 25. Anther length: About 2 mm. Anther shape: Lanceolate to elliptic. Anther color: Close to 14B. Pollen amount: Abundant. Pollen color: Close to 15C. Pistils: Quantity per flower: About 30. Pistil length: About 1 mm to 2 mm. Stigma shape: Rounded. Stigma color: Close to 5A. Fruits: Quantity: About seven to twelve per truss. Natural fruiting season: Plants develop fruit during the summer, early June until early July, in The Netherlands, ripening time considered mid to late season; fruiting is non-remontant. Postharvest longevity: About ten days at 7° C. Length: About 2 cm to 5 cm. Diameter: About 2 cm to 3.5 cm. Shape: Fruits are relatively medium to large and are conical in shape. Fruit weight per fruit, first quality: About 22.4 g. Fruit weight per plant, first quality: About 1,200 g. Firmness: Medium firm. Fragrance, taste: Pleasant; good balance between sweetness and acidity; aromatic. Luster: Uniformly glossy. Surface unevenness: Smooth. Color, surface: Close to 34A. Color, flesh: Close to 30A to 30B. Seed density: Medium. Achene position: Level with surface. Achene color: Close to 1A.

Disease and pest resistance: Plants of the new Strawberry have been observed to be moderately resistant to *Phytophthora cactorum* and *Podosphaera aphanis*. Plants of the new Strawberry have not been observed to be resistant to pests and other pathogens common to Strawberry plants.

It is claimed:

1. A new and distinct Strawberry plant named 'FF 1503' as illustrated and described.

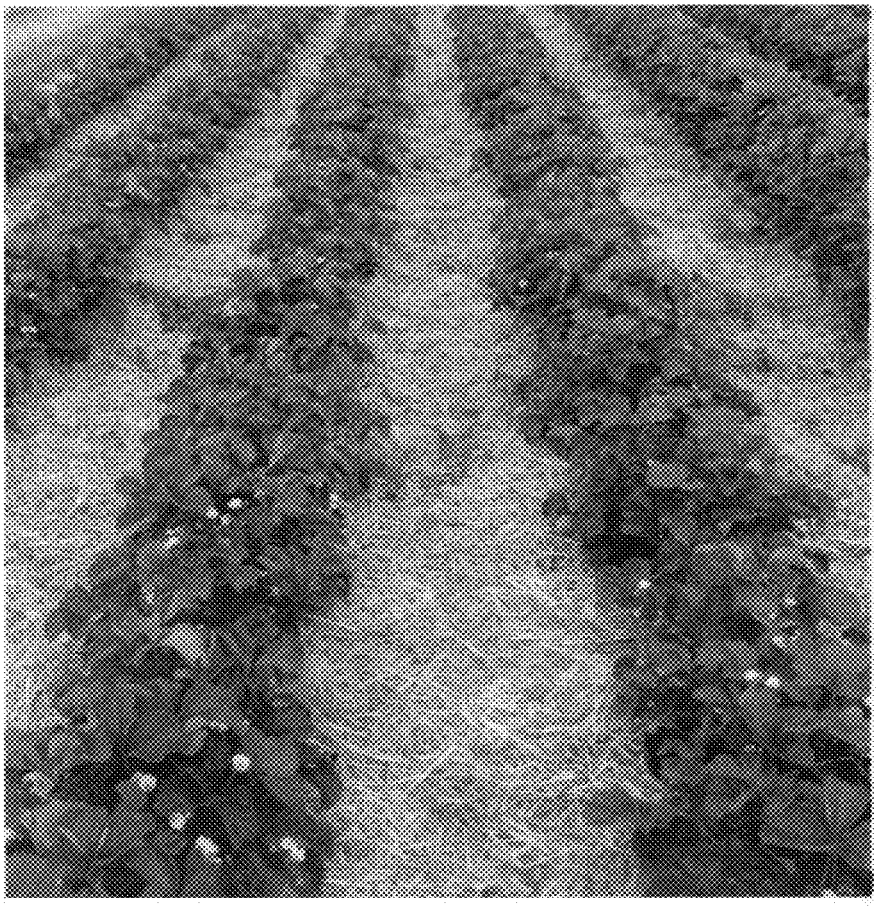

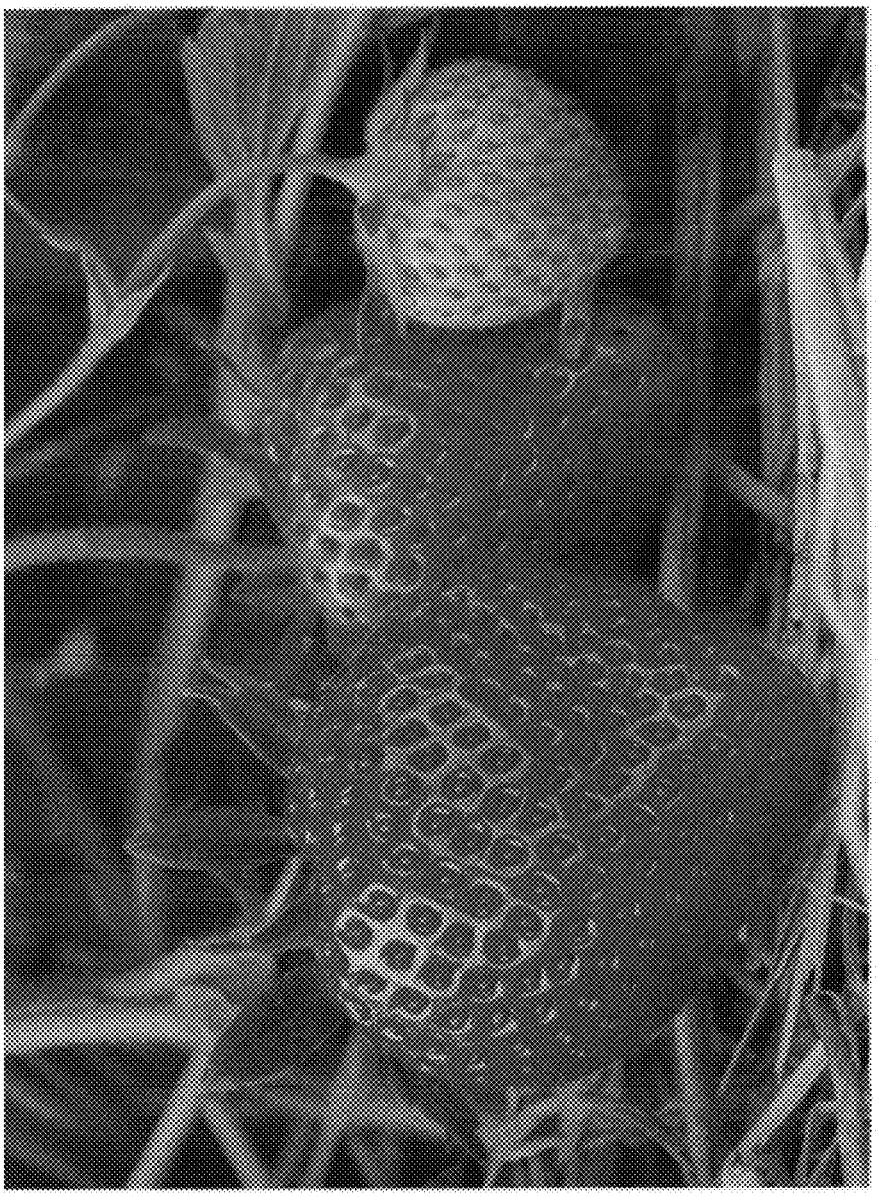

* * * * *